United States Patent
Castor et al.

(10) Patent No.: US 7,040,183 B2
(45) Date of Patent: May 9, 2006

(54) ARRANGEMENT FOR PASSIVE GAS SAMPLING

(75) Inventors: Rolf Castor, Hägersten (SE); Magnus Hallbäck, Bromma (SE)

(73) Assignee: Maquet Critical Care AB, Solna (SE)

( * ) Notice: Subject to any disclaimer, the term of this patent is extended or adjusted under 35 U.S.C. 154(b) by 192 days.

(21) Appl. No.: 10/686,983

(22) Filed: Oct. 16, 2003

(65) Prior Publication Data

US 2004/0093964 A1   May 20, 2004

(30) Foreign Application Priority Data

Nov. 20, 2002   (SE) .................................. 0203427

(51) Int. Cl.
*G01N 1/22* (2006.01)
*G01N 33/497* (2006.01)
*A61B 5/097* (2006.01)

(52) U.S. Cl. .................... 73/864.73; 73/23.3; 600/532; 600/543

(58) Field of Classification Search ............. 73/864.73, 73/863.41, 863.51, 863.57, 863.61, 864, 73/23.3; 600/532, 543; 128/204.22, 205.12
See application file for complete search history.

(56) References Cited

U.S. PATENT DOCUMENTS

| | | | | |
|---|---|---|---|---|
| 2,484,217 A | * | 10/1949 | Gardenier | 600/532 |
| 3,395,701 A | * | 8/1968 | Bartlett, Jr. et al. | 600/532 |
| 3,507,146 A | | 4/1970 | Campbell et al. | 600/532 X |
| 3,544,273 A | | 12/1970 | McConnaughey | 600/532 X |
| 4,270,564 A | * | 6/1981 | Blackburn et al. | 128/205.12 |
| 4,297,871 A | * | 11/1981 | Wright et al. | 73/23.3 |
| 5,355,893 A | | 10/1994 | Mick et al. | 600/532 |
| 5,443,075 A | | 8/1995 | Holscher | 600/538 |
| 5,625,189 A | * | 4/1997 | McCaul et al. | 250/343 |
| 5,826,577 A | * | 10/1998 | Perroz et al. | 600/532 |
| 6,306,098 B1 | | 10/2001 | Orr et al. | 128/200.26 |
| 6,358,215 B1 | * | 3/2002 | Ricciardelli | 600/532 |
| 6,450,968 B1 | * | 9/2002 | Wallen et al. | 600/532 |
| 2002/0183643 A1 | * | 12/2002 | Kuck et al. | 600/532 |
| 2004/0094154 A1 | * | 5/2004 | Castor et al. | 128/204.22 |
| 2004/0186391 A1 | * | 9/2004 | Pierry et al. | 600/532 |

FOREIGN PATENT DOCUMENTS

| | | |
|---|---|---|
| EP | 0 833 156 | 1/1998 |
| GB | 2 055 046 | 2/1981 |
| JP | 61-284257 | 12/1986 |

* cited by examiner

*Primary Examiner*—Thomas P. Noland
(74) *Attorney, Agent, or Firm*—Schiff Hardin LLP

(57) ABSTRACT

An arrangement for passive gas sampling of a breathing gas in a breathing system allows sampling during both inspiration and expiration. The arrangement has a tube-piece having a first connector for receiving an inspiratory gas flow, a second connector for delivering an expiratory gas flow and a third connector for delivering the inspiratory gas flow and receiving the expiratory gas flow, a first port arranged between the second connector and the third connector and connected to a measurement chamber, a second port arranged between the first connector and the third connector and connected to the measurement chamber and a third port arranged between the first connector and the second connector and connected to the measurement chamber. The tube-piece is formed such that when an inspiratory flow passes through the tube-piece, a flow is established principally between the first port, the measurement chamber and the second port, and that when an expiratory flow passes through the tube-piece a flow is established principally between the third port, the measurement chamber and the first port.

5 Claims, 2 Drawing Sheets

ARRANGEMENT FOR PASSIVE GAS SAMPLING

BACKGROUND OF THE INVENTION

1. Field of the Invention

The present invention relates to an arrangement for passive gas sampling of the type suitable for sampling a breathing gas.

2. Description of the Prior Art

In breathing systems such as ventilators and anesthetic apparatuses the breathing gas is analyzed regularly. This may be done directly in the main supply (with a so-called mainstream-analyzer) or by diverting a gas sample to a measuring chamber (so-called side stream-analyzer).

The diversion of the gas sample can be done actively by means of a pump or the like or passively, for example by creating a pressure variation between the pressure chamber's inlet and outlet. An example of the latter is described in U.S. Pat. No. 6,450,968.

SUMMARY OF THE INVENTION

An object of the present invention is to provide an alternative to known arrangements for passive gas sampling. A further object of the present invention is to provide an arrangement that is capable of sampling gas from breathing gas during both inspiration and expiration.

These objects are achieved in accordance with the present invention in an arrangement for passive gas sampling of a breathing gas in a breathing system, having a tube-piece with a first connector for receiving an inspiratory gas flow, a second connector for delivering an expiratory gas flow, and a third connector for delivering the inspiratory gas flow and receiving the expiratory gas flow. The arrangement further includes a first port disposed between the second connector and the third connector and connected to a measurement chamber, a second port disposed between the first connector and the third connector and also connected to the measurement chamber, and a third port disposed between the first connector and the second connector and also connected to the measurement chamber.

In a tube-piece with three connectors, for example a Y-piece in a breathing apparatus, there arise aerodynamic effects that cause turbulence and pressure variations. These can be exploited in order to passively sample gas from a breathing gas. These effects arise during both inspiration and expiration.

DESCRIPTION OF THE PREFERRED EMBODIMENTS

Figure 1:
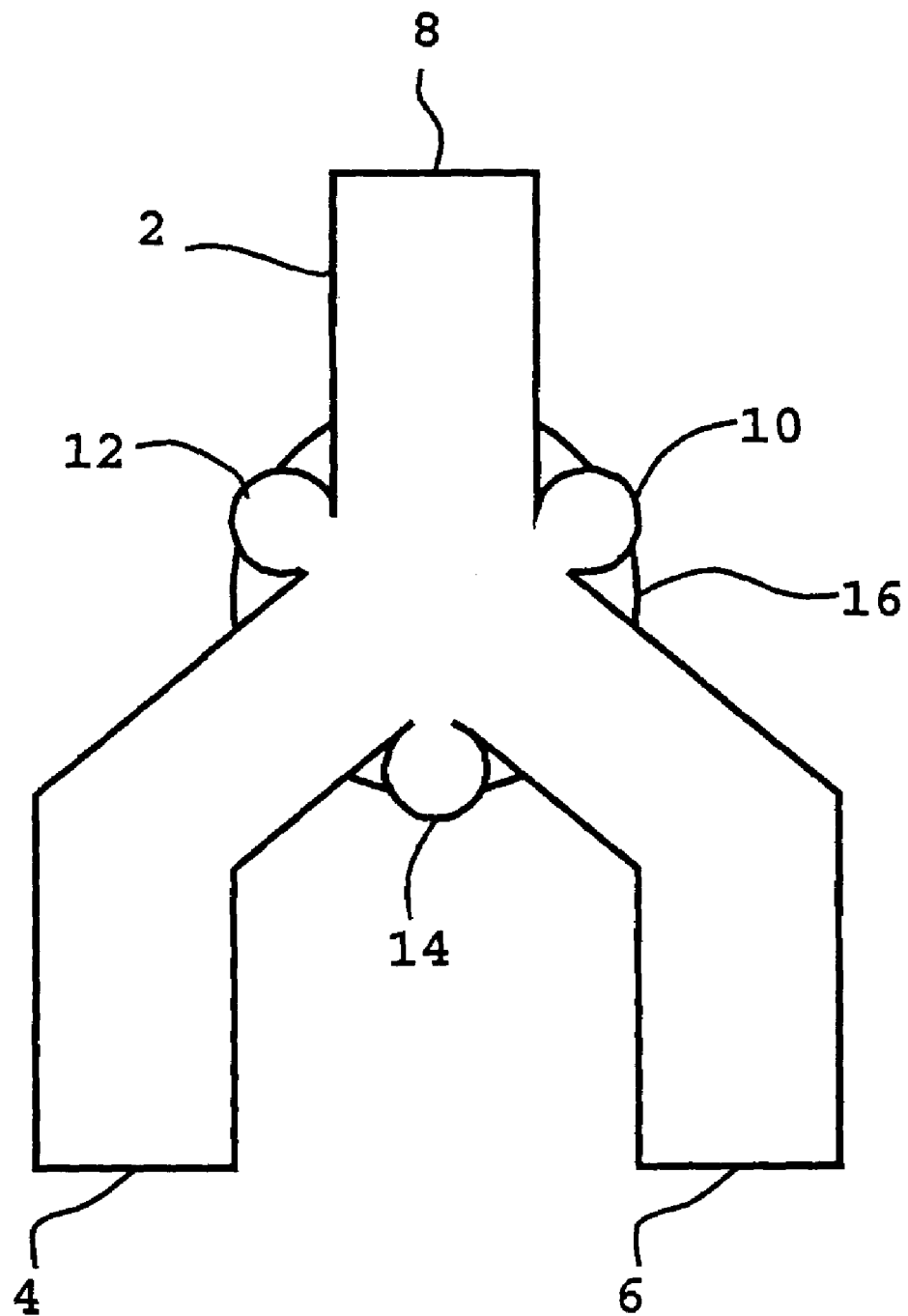
FIG. 1 shows an embodiment of an arrangement according to the invention.

An arrangement 2 according to the invention is shown in FIG. 1. The arrangement 2 is formed essentially of a tube-piece (for example a Y-piece) with a first connection 4 for receiving an inspiratory gas flow from a (not shown) breathing device; a second connector 6 for delivering an expiratory gas flow, and a third connector 8 for delivering the inspiratory gas flow and receiving the expiratory gas flow respectively to and from a (not shown) patient.

In order to divert a gas sample from and return a gas sample to the breathing gas flow in the arrangement 2, a first port 10 is arranged between the second connector 6 and the third connector 8, a second port 12 is arranged between the first connector 4 and the third connector 8, and a third port 14 is arranged between the first connector 4 and the second connector 6. All three ports 10, 12, 14 are connected to a measurement chamber 16 for the analysis of the gas sample. The analysis of the gas sample may be achieved according to any known analysis method, for example optically, electrochemically or acoustically.

The locations of the ports 10,12,14 and the design of the flow paths within the arrangement 2 fundamentally influence the level of effectiveness of the passive exchange of gas samples in the measurement chamber 16. The basic principle is, however, the same, that is the exploitation of aerodynamic effects. This shall now be described.

During inspiration breathing gas will flow through the arrangement 2 from the first connector 4 to the third connector 8. The first port 10 will in the present context lie essentially in the middle of the path for the breathing gas whilst at the same time turbulence generates a lower pressure at the second port 12. A gas sample therefore will flow essentially into the measurement chamber 16 through the first port 10 and contemporaneously with flow of the earlier gas sample from the measurement chamber 16 through the second port 12. The turbulence will even result in a weak flow into the measurement chamber 16 through the third port 14.

During expiration breathing gas will flow through the arrangement 2 from the third connector 8 to the second connector 6. The third port 14 will in the present context lie essentially in the middle of the path for the breathing gas, while at the same time turbulence generates a lower pressure at the first port 10. A gas sample therefore will flow essentially into the measurement chamber 16 through the third port 14 contemporaneously with flow of the earlier gas sample from the measurement chamber 16 through the first port 10. Turbulence will even result in a weak flow into the measurement chamber 16 through the second port 12.

The separations between the respective ports 10,12,14 and the measurement chamber 16 as well as the volume that they occupy should be as small as possible, having regard to the analysis method that is applied, in order to expedite the exchange of the gas sample.

Figure 2:
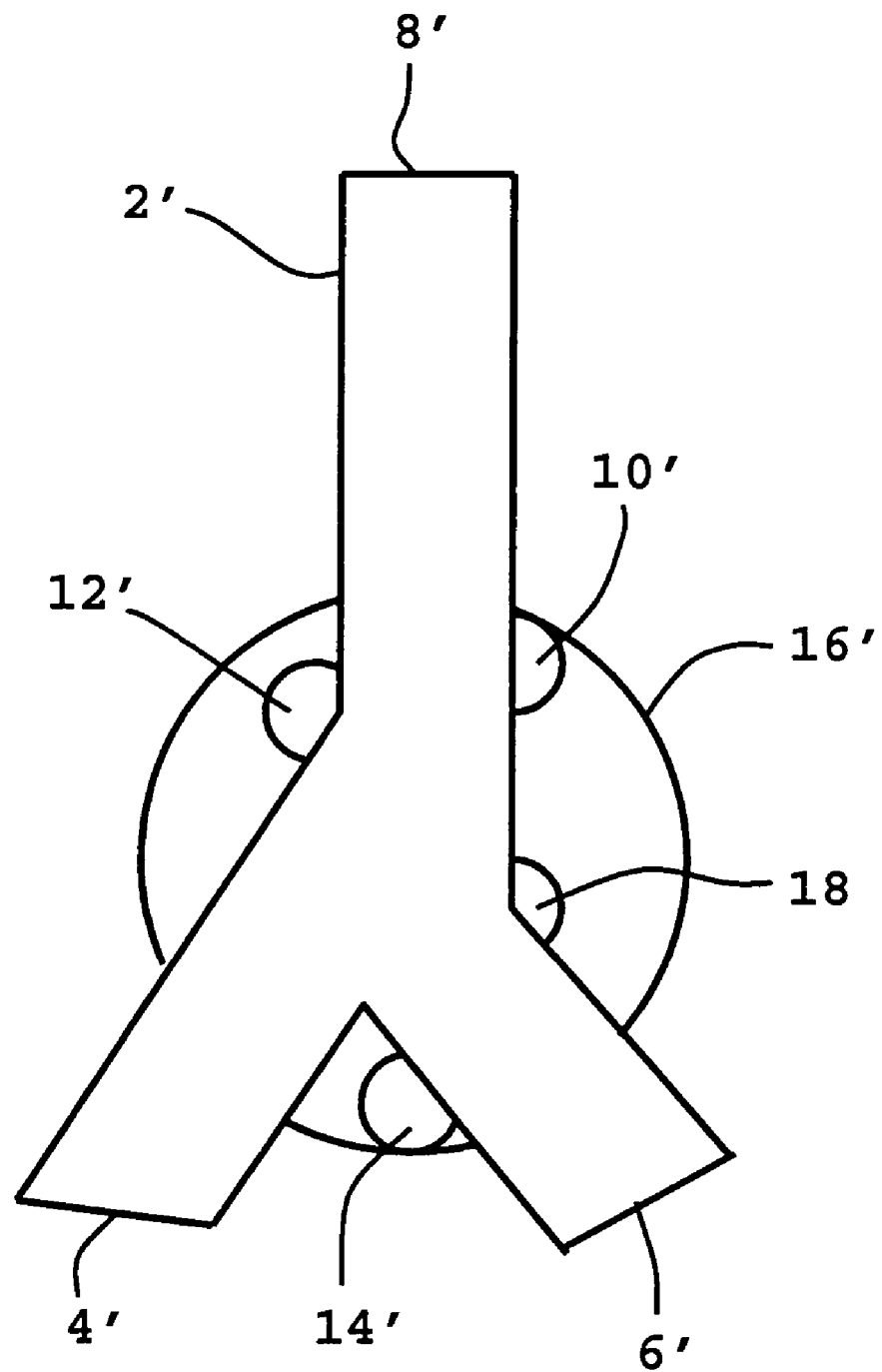
FIG. 2 shows an alternative embodiment of an arrangement according to the invention.

An alternative embodiment of an arrangement 2' according to the present invention is provided in FIG. 2.

The alternative embodiment is built upon the same principle for passive gas sampling as that of FIG. 1 except that in the alternative embodiment sampling during inspiration and expiration occurs through separate ports.

The arrangement 2' in the present case has a tube-piece with a first connection 4' for receiving an inspiratory gas flow from a (not shown) breathing device, a second connector 6' for delivering an expiratory gas flow and a third connector 8' for delivering the inspiratory gas flow and receiving the expiratory gas flow respectively to and from a (not shown) patient.

In order to divert a gas sample from and return a gas sample to the breathing gas flow in the arrangement 2' a first port 10' is arranged between the second connector 6' and the third connector 8', a second port 12' is arranged between the first connector 4' and the third connector 8', a third port 14' is arranged between the first connector 4' and the second connector 6', and a fourth port 18 is arranged between the second connector 6' and the third connector 8'. All four ports 10', 12', 14', 18 are connected to a measurement chamber 16' for the analysis of the gas sample.

As is shown in the FIG. 2, the arrangement 2' is asymmetric and therefore requires that the couplings to the inspiration tube and the expiration tube be made exactly according to that shown in FIG. 2 (the arrangement 2 of FIG. 1 is symmetric and therefore functions regardless of how it is coupled to the inspiration and the expiration tubes).

During inspiration breathing gas will flow through the arrangement 2' from the first connector 4' to the third connector 8'. The first port 10' will in the present context lie essentially in the middle of the path for the breathing gas whilst at the same time turbulence generates a lower pressure at the second port 12'. A gas sample therefore will flow essentially into the measurement chamber 16' through the first port 10 and contemporaneously with flow of the earlier gas sample from the measurement chamber 16' through the second port 12'.

During expiration breathing gas will flow through the arrangement 2' from the third connector 8' to the second connector 6'. The third port 14' will in the present context lie essentially in the middle of the path for the breathing gas, while at the same time turbulence generates a lower pressure at the fourth port 18. A gas sample therefore will flow essentially into the measurement chamber 16' through the third port 14' contemporaneously with flow of the earlier gas sample from the measurement chamber 16' through the fourth port 18.

An advantage with the arrangement 2' according to the alternative embodiment is that no mixing of gases from the different phases will occur in the respective ports (i.e., only inspiratory gas will flow through the first port 10' and the second port 12' while only expiratory gas will flow through the third port 14' and the fourth port 18).

An important advantage with the present arrangement 2 is that one may measure the gas with an analyzer during both inspiration and expiration.

A further valuable advantage is that the arrangement 2 does not provide any increase in resistance to the flow of breathing gas in the flow paths that is otherwise usual when passive gas sampling is desired.

Although modifications and changes may be suggested by those skilled in the art, it is the intention of the inventors to embody within the patent warranted hereon all changes and modifications as reasonably and properly come within the scope of their contribution to the art.

We claim as our invention:

1. An arrangement for passive gas sampling of a breathing gas in a breathing system, comprising:
    a tube-piece having a first connector adapted to receive an inspiratory gas flow, a second connector adapted to deliver an expiratory gas flow, and a third connector adapted to deliver the inspiratory gas flow and to receive the expiratory gas flow;
    a single measurement chamber associated with said tube-piece; and
    said tube-piece further having a first port disposed between said second connector and said third connector and connected to, and permanently open to, said measurement chamber, a second port disposed between said first connector and said third connector and connected to, and permanently open to, said measurement chamber and a third port disposed between said first connector and said second connector and connected to, and permanently open to, said measurement chamber.

2. An arrangement as claimed in claim 1 wherein said tube-piece has permenently existing flow paths therein repectively structurally configured to establish gas flow primarily between said first port and said measurement chamber and said second port when said inspiratory gas flow passes through said tube-piece, and to establish a gas flow primarily between said third port, said measurement chamber and said first port when said expiratory gas flow passes through said tube-piece.

3. An arrangement as claimed in claim 1 wherein said tube-piece comprises a fourth port disposed between said second connector and said third connector and connected to said measurement chamber.

4. An arrangement as claimed in claim 3 wherein said tube-piece has permanetly existing flow paths therein to respectively structurally establish a gas flow primarily between said first port, said measurement chamber and said second port when said inspiratory gas flow passes through said tube-piece, and to establish a gas flow primarily between said third port, said measurement chamber and said fourth port when said expiratory gas flow passes through said tube-piece.

5. An arrangement as claimed in claim 1 wherein said measurement chamber is cylindrical.

* * * * *